US011858871B2

(12) United States Patent
Gillespie

(10) Patent No.: US 11,858,871 B2
(45) Date of Patent: Jan. 2, 2024

(54) RENEWABLE METHANE PRODUCTION MODULE

(71) Applicant: SOUTHERN GREEN GAS LIMITED, Melbourne (AU)

(72) Inventor: Rohan Gillespie, Melbourne (AU)

(73) Assignee: SOUTHERN GREEN GAS LIMITED, Melbourne (AU)

( * ) Notice: Subject to any disclaimer, the term of this patent is extended or adjusted under 35 U.S.C. 154(b) by 111 days.

(21) Appl. No.: 17/256,132

(22) PCT Filed: May 30, 2019

(86) PCT No.: PCT/AU2019/050546
§ 371 (c)(1),
(2) Date: Dec. 24, 2020

(87) PCT Pub. No.: WO2020/000020
PCT Pub. Date: Jan. 2, 2020

(65) Prior Publication Data
US 2021/0221753 A1    Jul. 22, 2021

(30) Foreign Application Priority Data

Jun. 28, 2018  (AU) ................................ 2018902332
Aug. 29, 2018  (AU) ................................ 2018903181

(51) Int. Cl.
*C07C 1/12*    (2006.01)
*C25B 9/65*    (2021.01)
(Continued)

(52) U.S. Cl.
CPC ............ *C07C 1/12* (2013.01); *B01D 53/1418* (2013.01); *C25B 1/04* (2013.01); *C25B 9/65* (2021.01);
(Continued)

(58) Field of Classification Search
CPC .... C07C 1/12; C25B 1/04; C25B 9/65; B01D 2257/504; B01D 2257/80; Y02P 20/129; Y02P 20/133
See application file for complete search history.

(56) References Cited

U.S. PATENT DOCUMENTS

2012/0198884 A1    8/2012  Golben
2020/0010771 A1    1/2020  Yoon

FOREIGN PATENT DOCUMENTS

AU    2013101029 A4    9/2013
AU    2014200989 A1    10/2014
(Continued)

OTHER PUBLICATIONS

ES Patent First Examination Report dated Feb. 9, 2022 as received in Application No. 202090068.
(Continued)

*Primary Examiner* — Jafar F Parsa
(74) *Attorney, Agent, or Firm* — Maschoff Brennan

(57) ABSTRACT

A renewable methane production module generally includes a water capture generator designed for directly capturing water from atmosphere to provide water in a liquid form, an electrolyser operatively coupled to the water capture generator for electrolysis of the liquid water to produce hydrogen and a reactor operatively coupled to the electrolyser for reacting the hydrogen with carbon dioxide at to produce renewable methane. Associated methods permit methane to be produced using the renewable methane production module.

15 Claims, 4 Drawing Sheets

(51) Int. Cl.
  *B01D 53/14* (2006.01)
  *C25B 1/04* (2021.01)
(52) U.S. Cl.
  CPC .. *B01D 2253/204* (2013.01); *B01D 2257/504* (2013.01); *B01D 2257/80* (2013.01); *B01D 2258/06* (2013.01)

(56) References Cited

FOREIGN PATENT DOCUMENTS

| | | | |
|---|---|---|---|
| DE | 102014217462 A1 | 3/2016 | |
| GB | 2552010 A * | 1/2018 | ............... C10G 2/32 |
| GB | 2552010 A | 1/2018 | |
| WO | 2019/093518 A1 | 5/2019 | |

OTHER PUBLICATIONS

ES Patent Second Examination Report dated Jun. 8, 2022 as received in Application No. 202090068.

\* cited by examiner

RENEWABLE METHANE PRODUCTION MODULE

TECHNICAL FIELD

The present invention relates broadly to a method of producing renewable methane, and a renewable methane production system. The invention further relates broadly to a renewable methane production module and relates particularly, although not exclusively, to a plurality of co-located production modules together forming a renewable methane production plant. The invention also relates broadly to a method of producing hydrogen, and a hydrogen production system.

BACKGROUND

It is known in a Sabatier reactor to react carbon dioxide with hydrogen to produce methane. The carbon dioxide may be recovered from atmosphere, for example in a direct air capture plant. The hydrogen may be obtained by the electrolysis of water with the electrolyser being powered by a renewable energy source, such as solar-derived power. The prior art of Australian patent no. 2014200989 exemplifies this method for producing methane. This Australian patent and other technologies in this field suffer from at least the following problems:
  i) the electrolyser requires a readily-available source of liquid water for electrolysis in the production of hydrogen;
  ii) the production of hydrogen and/or carbon dioxide requires power derived from non-renewable sources and as such the methane is not deemed renewable.

SUMMARY OF INVENTION

According to a first aspect of the present invention there is provided a renewable methane production module comprising:
  a water capture generator designed for directly capturing water from atmosphere to provide water in a liquid form;
  an electrolyser operatively coupled to the water capture generator for receiving the liquid water, the electrolyser being effective in electrolysis of the liquid water to produce hydrogen;
  a reactor operatively coupled to the electrolyser for receiving the hydrogen and reacting it with carbon dioxide to produce renewable methane.

Preferably the water capture generator includes an absorbent material designed to be exposed to atmosphere for directly absorbing water from the atmosphere onto the absorbent material. More preferably the water capture generator also includes heating means designed to adsorb heat from a renewable energy source and transfer it to the absorbent material to release the absorbed water from the absorbent material to provide the liquid water for the electrolyser.

Preferably the renewably methane production module also comprises an electricity generating assembly powered by a renewable energy source, said electricity generating assembly configured to provide electricity for powering the electrolyser in electrolysis of the atmospheric water in the production of hydrogen. More preferably the electricity generating assembly includes a plurality of solar panels operatively coupled to the electrolyser for powering it. Still more preferably the solar panels are coupled to the electrolyser via an inverter. Alternatively the solar panels are directly coupled to the electrolyser.

Preferably the solar panels are in the form of solar photovoltaic (PV) panels arranged in an elongate bank of panels. Alternatively the solar panels are in the form of printed solar membranes. More preferably the bank of solar PV panels are located in two (2) rows on respective of opposing faces of a solar framework structure which is oriented in a generally magnetic North to South direction. Still more preferably the solar framework structure is in cross-section shaped in the form of an isosceles triangle having each of the two (2) rows of PV panels mounted to respective of leg-sides of the solar framework structure for increased solar exposure for said solar panels.

Preferably the renewable methane production module also comprises a carbon dioxide extractor for extracting carbon dioxide from atmosphere. More preferably the carbon dioxide extractor is configured for directly capturing carbon dioxide from atmosphere using a metal-organic framework (MOF) or other absorbent structure capable of directly absorbing carbon dioxide from the atmosphere.

Preferably the reactor is an exothermic reactor for reacting hydrogen from the electrolyser with carbon dioxide from the carbon dioxide extractor to produce renewable methane in a Sabatier reaction. More preferably the exothermic reactor is operatively coupled to a heat exchanger designed to exchange heat derived from the production of renewable methane with the carbon dioxide extractor to heat the absorbent structure of said extractor to release the absorbed carbon dioxide from the absorbent structure. Alternatively the carbon dioxide extractor is operatively coupled to the electricity generating module for heating of the absorbent structure to release the absorbed carbon dioxide. Still more preferably the heat exchanger is operatively coupled to the electrolyser wherein steam produced from the exothermic reactor exchanges heat with the carbon dioxide extractor to promote the release of the absorbed carbon dioxide wherein said steam is condensed to provide liquid water to the electrolyser for the production of hydrogen.

Preferably the water capture generator includes at least one pair of water capture panels mounted to a water capture framework structure associated with the solar framework structure. More preferably the water capture framework structure is of substantially the same configuration and aligned with the solar framework structure for increased solar exposure of the pair of water capture panels which are located on respective opposing sides of the water capture framework structure.

Alternatively the water capture generator is configured for directly capturing water from atmosphere using a MOF or other absorbent structure capable of directly absorbing water from the atmosphere. In this variation the heat exchanger associated with the exothermic reactor is operatively coupled to the water capture generator to heat the absorbent structure of said water generator to release the absorbed water from the absorbent material. In this embodiment the water capture generator is operatively coupled to the carbon dioxide extractor wherein dehumidified air from the water capture generator is received by the carbon dioxide extractor for extracting carbon dioxide from the dehumidified air. In this case the carbon dioxide extractor is operatively coupled to the heat exchanger associated with the exothermic reactor to heat the absorbent structure of the carbon dioxide extractor to release the absorbed carbon dioxide. Alternatively the absorbed carbon dioxide is released from the absorbent structure by heating it using electricity provided by the electricity generating module.

Preferably the renewable methane production module includes an equipment platform at which at least the electrolyser, the reactor, the heat exchanger, and the carbon dioxide extractor are located. More preferably the equipment platform is located alongside the solar framework structure and the water capture framework structure.

Preferably the carbon dioxide extractor is operatively coupled to one or more batteries charged by the electricity derived from the plurality of solar panels. More preferably the carbon dioxide extractor includes pumps and/or fans powered by electricity supplied from said one or more batteries.

Preferably the renewable methane production module is one of a plurality of said production modules. More preferably said production modules are co-located and together form a renewable methane production plant.

According to a second aspect of the present invention there is provided a method of producing renewable methane comprising the steps of:
  directly capturing water from air to provide water in a liquid form;
  producing hydrogen by electrolysis of the liquid water;
  reacting the hydrogen with carbon dioxide to produce renewable methane.

Preferably the step of directly capturing water involves exposing air to an absorbent material to absorb water from the air onto the absorbent material. More preferably said step also involves i) releasing the absorbed water from the absorbent material by heating it, and ii) condensing the released water by cooling it to provide the liquid water. Even more preferably the absorbed water is released from the absorbent material using a) solar energy, and/or b) waste heat from the reaction between hydrogen and carbon dioxide to heat the absorbent material. Alternatively the step of directly capturing water involves refrigeration of air to release water from the air to provide the liquid water.

Preferably the step of producing hydrogen involves: i) generating electricity via a renewable energy source, and ii) using the electricity to power the electrolysis of the liquid water for the production of hydrogen.

Preferably the step of reacting the hydrogen with carbon dioxide involves a preliminary step of either extracting carbon dioxide from air or obtaining carbon dioxide from a biogas reactor. More preferably the extraction of carbon dioxide from air involves directly capturing carbon dioxide from air using solar energy and/or waste heat from the reaction between hydrogen and carbon dioxide.

Preferably the method also comprises the step of recirculating liquid water produced from the reaction between hydrogen and carbon dioxide for electrolysis in the production of hydrogen. More preferably the recirculated liquid water is combined with the liquid water directly captured from air for electrolysis in the production of hydrogen.

According to a third aspect of the invention there is provided a renewable methane production system comprising:
  a water capture module for directly capturing water from air to provide water in a liquid form;
  an electrolysis module for electrolysis of the liquid water to produce hydrogen;
  an exothermic reactor for reacting the hydrogen with carbon dioxide to produce renewable methane.

Preferably the water capture module includes an absorbent unit including an absorbent material designed to be exposed to air for absorbing water from the air onto the absorbent material. More preferably the water capture module also includes i) a heating unit designed to heat the absorbent material to release the absorbed water from the absorbent material, ii) a condensing unit designed to condense the released water by cooling it to provide the liquid water. Even more preferably the heating unit includes a) a solar heating unit, and/or b) a heat recovery unit associated with the exothermic reactor for recovering waste heat from the exothermic reaction, being arranged for heating of the absorbent material.

Preferably the electrolysis module includes an electricity generating module powered by a renewable energy source, said electricity generating module configured to provide electricity for powering the electrolysis of the liquid water in the production of hydrogen.

Preferably the production system also comprises a carbon dioxide module for either extracting carbon dioxide from air or obtaining carbon dioxide from a biogas reactor. More preferably the carbon dioxide module includes a carbon dioxide capture module for directly capturing carbon dioxide from air.

Preferably the production system also comprises a water recirculation module arranged to recirculate liquid water produced from the exothermic reactor to the electrolysis module for the production of hydrogen.

According to a fourth aspect of the invention there is provided a method of producing hydrogen comprising the steps of:
  directly capturing water from air to provide water in a liquid form;
  producing hydrogen by electrolysis of the liquid water.

Preferably the step of directly capturing water involves exposing air to an absorbent material to absorb water from the air onto the absorbent material. More preferably said step also involves i) releasing the absorbed water from the absorbent material by heating it, and ii) condensing the released water by cooling it to provide the liquid water. Even more preferably the absorbed water is released from the absorbent material using solar energy to heat it.

Preferably the step of producing hydrogen involves: i) generating electricity via a renewable energy source, and ii) using the electricity to power the electrolysis of the directly captured water for the production of hydrogen.

Preferably the method also comprises the step of purifying the hydrogen produced from the electrolysis to provide hydrogen fuel. More preferably the step of purifying the hydrogen involves filtering the hydrogen produced by electrolysis to obtain the hydrogen fuel at purity levels required for fuel cell vehicles. Alternatively or additionally the purifying step involves drying the hydrogen.

According to a fifth aspect of the invention there is provided a hydrogen production system comprising:
  a water capture module for directly capturing water from air to provide water in a liquid form;
  an electrolysis module for electrolysis of the liquid water to produce hydrogen.

Preferably the water capture module includes an absorbent unit including an absorbent material designed to be exposed to air for absorbing water from the air onto the absorbent material. More preferably the water capture module also includes i) a heating unit designed to heat the absorbent material to release the absorbed water from the absorbent material, and ii) a condensing unit designed to condense the released water by cooling it to provide the liquid water. Even more preferably the heating unit includes a solar heating unit for heating of the absorbent material.

Preferably the electrolysis module includes an electricity generating module powered by a renewable energy source, said electricity generating module configured to provide electricity for powering the electrolysis of the directly captured water in the production of hydrogen.

Preferably the production system also comprises a purifying module for purifying the hydrogen from the electrolysis module to provide hydrogen fuel. More preferably the purifying module includes a purifying filter for filtering the hydrogen produced by the electrolysis module to obtain the hydrogen fuel at purity levels required for fuel cell vehicles. Alternatively or additionally the purifying module includes a dryer for drying the hydrogen.

BRIEF DESCRIPTION OF DRAWINGS

In order to achieve a better understanding of the nature of the present invention a preferred embodiment of a renewable methane production module as well as a method and system for the production of renewable methane or hydrogen will now be described, by way of example only, with reference to the accompanying drawings in which.

DETAILED DESCRIPTION

Figure 1:
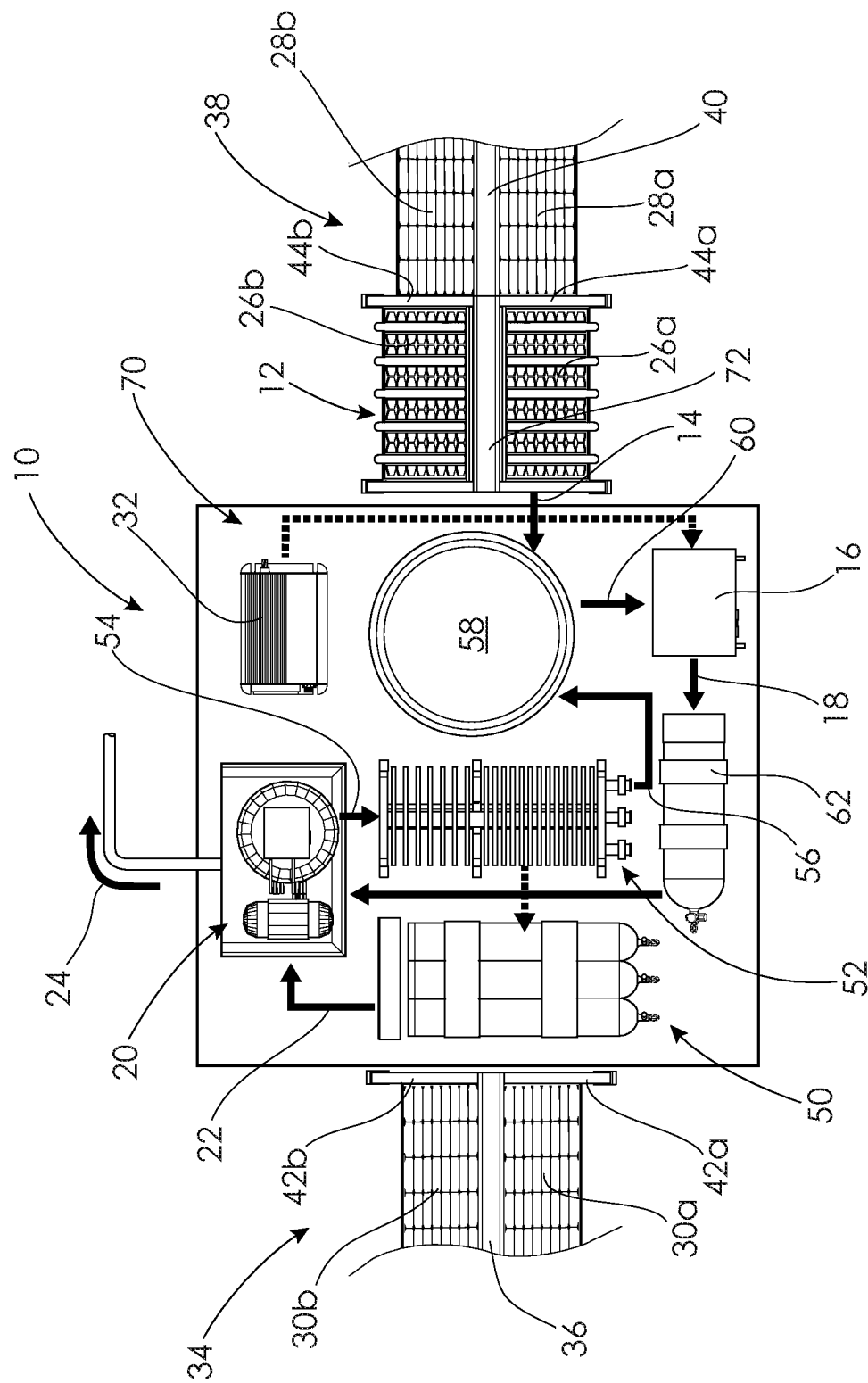
FIG. 1 is an enlarged plan view of part of an embodiment of a renewable methane production module according to one aspect of the invention.
Figure 2:
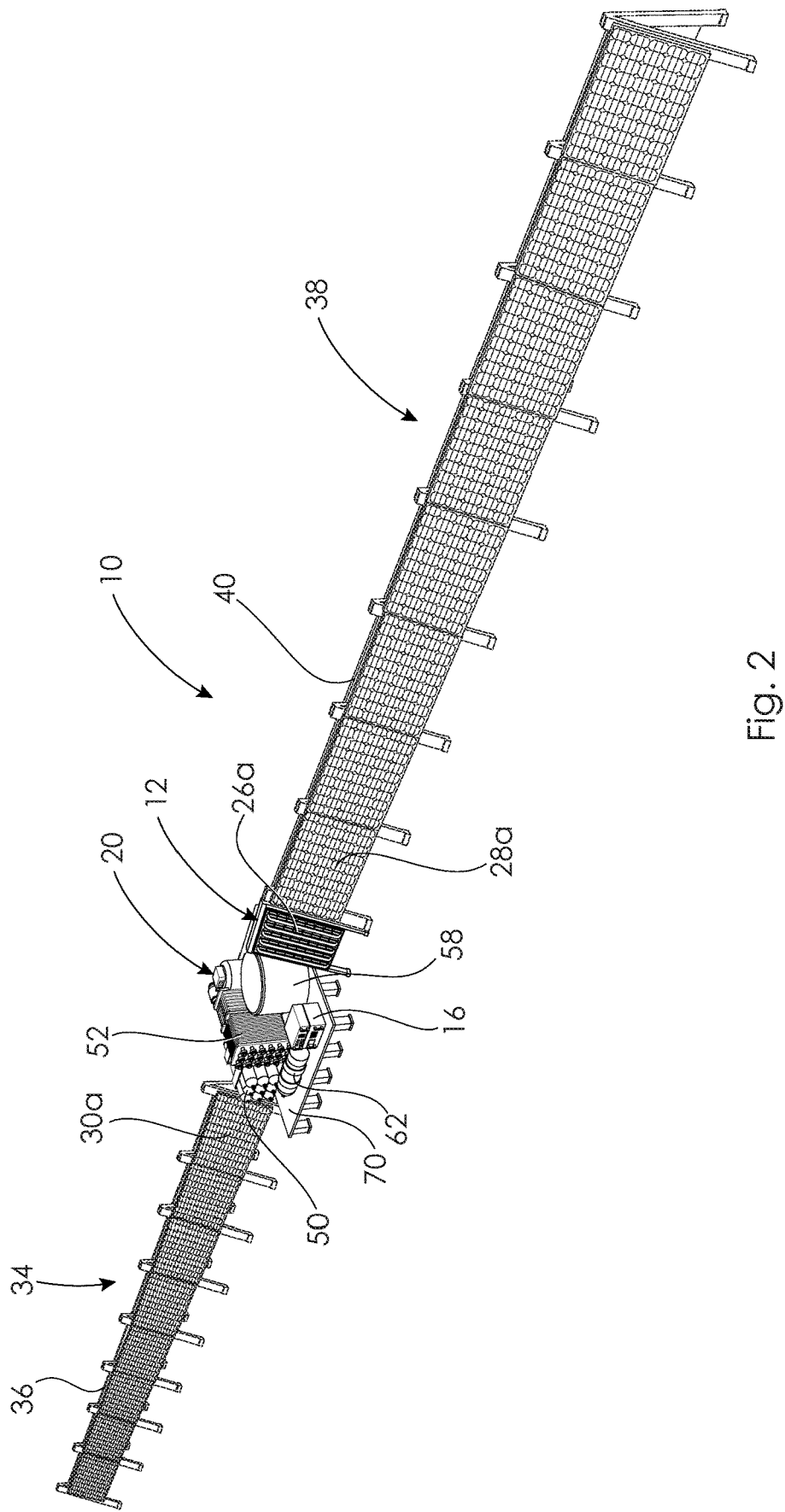
FIG. 2 is a perspective view of the renewable methane production module of the embodiment of FIG. 1 shown in its entirety.

As seen in FIGS. 1 and 2 there is according to one aspect of the invention a renewable methane production module 10 generally comprising:
1. a water capture generator 12 designed for directly capturing water from atmosphere to provide water in a liquid form at 14;
2. an electrolyser 16 operatively coupled to the water capture generator 12 for electrolysis of the liquid water to produce hydrogen at 18;
3. a reactor 20 operatively coupled to the electrolyser 16 for reacting the hydrogen with carbon dioxide at 22 to produce renewable methane at 24.

In this embodiment the water capture generator 12 includes a pair of water capture panels 26a and 26b each including an absorbent material (not shown) designed to be exposed to atmosphere for directly absorbing water from the atmosphere on to the absorbent material. Each of the water capture panels 26a/b of this embodiment also includes heating means (not shown) designed to absorb heat from a renewable energy source such as solar energy and transfer it to the absorbent material to release the absorbed water to provide water in a liquid form for the electrolyser 16. In this example the absorbent material and solar heating means are together integrated within the water capture panels 26a/b.

In this embodiment the renewable methane production module 10 also comprises an electricity generating assembly (not designated) powered by a renewable energy source such as solar energy. The electricity generating assembly of this example includes a plurality of solar panels such as 28a/28b and 30a/30b operatively coupled to an inverter 32 for production of electricity for powering the electrolyser 16. In the absence of an inverter, the solar panels are directly coupled to the electrolyser 16. The solar panels such as 28a/b and 30a/b are in the form of solar photovoltaic (PV) panels arranged in an elongate bank of panels. In this case the solar PV panels are arranged in a first elongate bank of panels 34 in two rows such as 30a and 30b respectively on opposing faces of a first solar framework structure 36. The solar PV panels are also located in a second elongate bank of panels 38 in two rows of panels such as 28a and 28b respectively on opposing faces of a second solar framework structure 40. The first and second solar framework structures 36 and 40 are aligned with one another and oriented in a generally magnetic North to South direction. Each of the first and second solar framework structures 36/40 is in cross-section shaped in the form of an isosceles triangle having each of the two rows of PV panels such as 30a/b and 28a/b mounted to respective of leg-sides such as 42a/b and 44a/b of the first and second solar framework structures 36 and 40 respectively. It will be understood that this North to South orientation combined with the triangular solar framework structures 36 and 40 provides increased exposure of the solar PV panels 30a/b and 28a/b to sunlight.

In this embodiment the renewal methane production module 10 also comprises a carbon dioxide extractor 50 for extracting carbon dioxide from atmosphere. The carbon dioxide extractor 50 directly captures carbon dioxide from atmosphere using a metal-organic framework (MOF) or other absorbent structure (not shown). In this example the carbon dioxide extractor 50 is operatively coupled to a heat exchanger 52 to heat the absorbent structure of the carbon dioxide extractor 50 to release the absorbed carbon dioxide from the absorbent structure. The released carbon dioxide at 22 is fed to the reactor 20 to react with the hydrogen in producing the renewable methane at 24.

In this example the reactor 20 is an exothermic reactor which produces renewable methane in a Sabatier reaction. The exothermic Sabatier reactor 20 is operatively coupled to the heat exchanger 52 where steam at 54 from the Sabatier reactor 20 exchanges heat with the carbon dioxide extractor 50 to release the absorbed dioxide from the absorbent structure associated with the carbon dioxide extractor 50. The steam on exchanging its heat at the heat exchanger 52 condenses to provide return liquid water at 56 to be circulated to the electrolyser 16 for the production of hydrogen.

In this embodiment the renewable methane production module 10 comprises a water storage vessel 58 designed to store both the released water 14 from the water capture generator 12, and the return liquid water 56 from the heat exchanger 52. The water storage vessel 58 supplies the liquid water at 60 to the electrolyser 16 for the production of hydrogen. It is expected that the water capture generator 12 will supply liquid water to the storage vessel 58 predominantly during daylight hours when the absorbed water from the absorbent material of the water capture panels 26a/b is released on solar heating. The supply of the return liquid water 56 to the storage vessel 58 will occur during production of renewable methane at the Sabatier reactor 20 whilst steam is being condensed at the heat exchanger 52.

In this embodiment the renewable methane production module 10 further comprises one or more hydrogen storage vessels 62 arranged to receive the hydrogen 18 produced from the electrolyser 16. The hydrogen storage vessel 62 is intended to provide an extended supply of hydrogen to the Sabatier reactor 20 for continued operation without being limited to daylight hours during which water is predominantly released from the water capture generator 12. That is, the hydrogen storage vessel 62 provides an effective buffer in storing hydrogen for supply to the Sabatier reactor 20. This hydrogen storage capability is consistent with operation of the electrolyser 16 during predominantly daylight hours when powered by the solar PV panels such as 28a/b and 30a/b and the associated inverter 32.

In this configuration the renewable methane production module 10 includes an equipment platform 70 at which the electrolyser 16, the Sabatier reactor 20, the inverter 32, the carbon dioxide extractor 50, the heat exchanger 52, the water storage vessel 58 and the hydrogen storage vessel 62 are located. The equipment platform 70 is in this embodiment located between the first and second solar framework structures 36 and 40. The pair of water capture panels 26a/b are mounted to a water capture framework structure 72 located adjacent the equipment platform 70. In this example the water capture framework structure 72 is of substantially the same configuration as and aligned with the second solar framework structure 40. It will be understood that this configuration provides the pair of water capture modules 26a/b with increased solar exposure in a similar manner to the solar PV panels such as 28a/b.

The carbon dioxide extractor 50 of this embodiment may be operatively coupled to one or more batteries (not shown) for extended operation without being limited to sunlight hours. In this configuration the inverter 32 is arranged to provide electricity for charging of the batteries. The electricity produced from the batteries may be used predominantly outside daylight hours for not only heating the MOF or other absorbent structure of the carbon dioxide extractor 50 for releasing carbon dioxide but also to power pumps and/or fans (not shown) associated with the carbon dioxide extractor 50. The carbon dioxide extractor 50 is otherwise powered during daylight hours by the solar PV panels such as 28a/b and 30a/b via the associated inverter such as 32. This means the carbon dioxide extractor can potentially operate 24/7 in producing carbon dioxide for supply to the Sabatier reactor 20 which likewise can operate around the clock.

Figure 3:
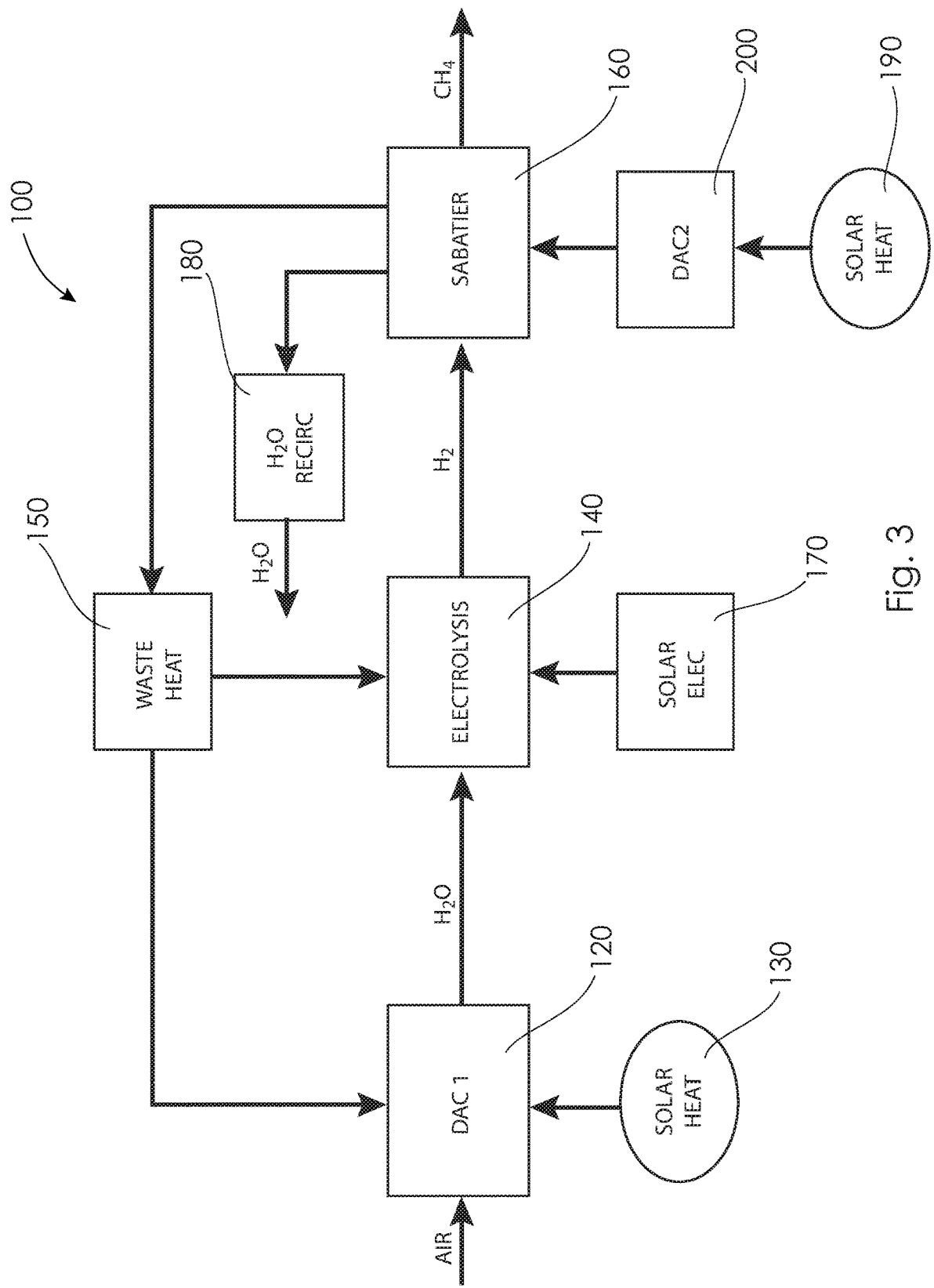
FIG. 3 is a schematic of a process flow sheet for a method and system for the production of renewable methane according to another aspect of the invention.

As seen in FIG. 3 there is according to another aspect of the invention a renewable methane production system 100 generally comprising:
1. a water capture module 120 for directly capturing water from air to provide water in a liquid form;
2. an electrolysis module 140 for electrolysis of the liquid water to produce hydrogen;
3. an exothermic reactor 160 for reacting the hydrogen from the electrolysis module 140 with carbon dioxide to produce renewable methane.

In this embodiment the water capture module 120 is in the form of a direct air capture module including a metal-organic framework (MOF) or other absorbent designed to capture or absorb water from the air. The MOF is the absorbent material within an absorbent unit of the water capture module 120. The water capture module 120 also includes i) a heating unit (not shown) designed to heat the MOF to release the absorbed water, and ii) a condensing unit (not shown) designed to condense the water released from the MOF by cooling of the released water to provide the liquid water for the electrolysis module 140. In this example the heating unit includes a) a solar heating unit 130, and/or b) a heat recovery unit 150 associated with the exothermic reactor 160 for recovering waste heat from the associated exothermic reaction, in both cases the heating unit being arranged for heating of the MOF.

In this embodiment the electrolysis module 140 includes an electricity generating module 170 powered by a renewable energy source, such as solar energy arranged to power an electricity generator (not shown) configured to provide electricity for powering the electrolysis module 140 for the production of hydrogen from the liquid water. It will be understood that the electrolysis module 140 may be powered by other renewable energy sources including but not limited to wind, wave, or tidal sources. The production system 100 of this embodiment also comprises a water recirculation module 180 arranged to recirculate liquid water produced from the exothermic reactor 160 to the electrolysis module 140 for the production of hydrogen.

In this embodiment the production system 100 also comprises a carbon dioxide module 200 for extracting carbon dioxide from air. The carbon dioxide module is based on MOF technology with the absorbent material designed to absorb carbon 200 dioxide from the air. The carbon dioxide capture module 200, in a similar manner to the water capture module 120, heats the absorbent material such as the MOF via a solar heating unit 190. Alternatively the carbon dioxide may be obtained from a biogas reactor. In either case the carbon dioxide combines with hydrogen in the exothermic reactor 160 for the production of renewable methane. In this example this reaction is a Sabatier reaction where, under the influence of a suitable catalyst, carbon dioxide reacts with hydrogen to produce renewable synthetic methane.

In a further aspect of the invention, in the context of the renewable methane production system 100, there is a method of producing renewable methane comprising the general steps of:
1. directly capturing water from air at the water capture module 120 to provide water in a liquid form;
2. producing hydrogen by electrolysis of liquid water at the electrolysis module 140;
4. reacting the hydrogen with carbon dioxide to produce renewable methane at the exothermic reactor 160.

Figure 4:
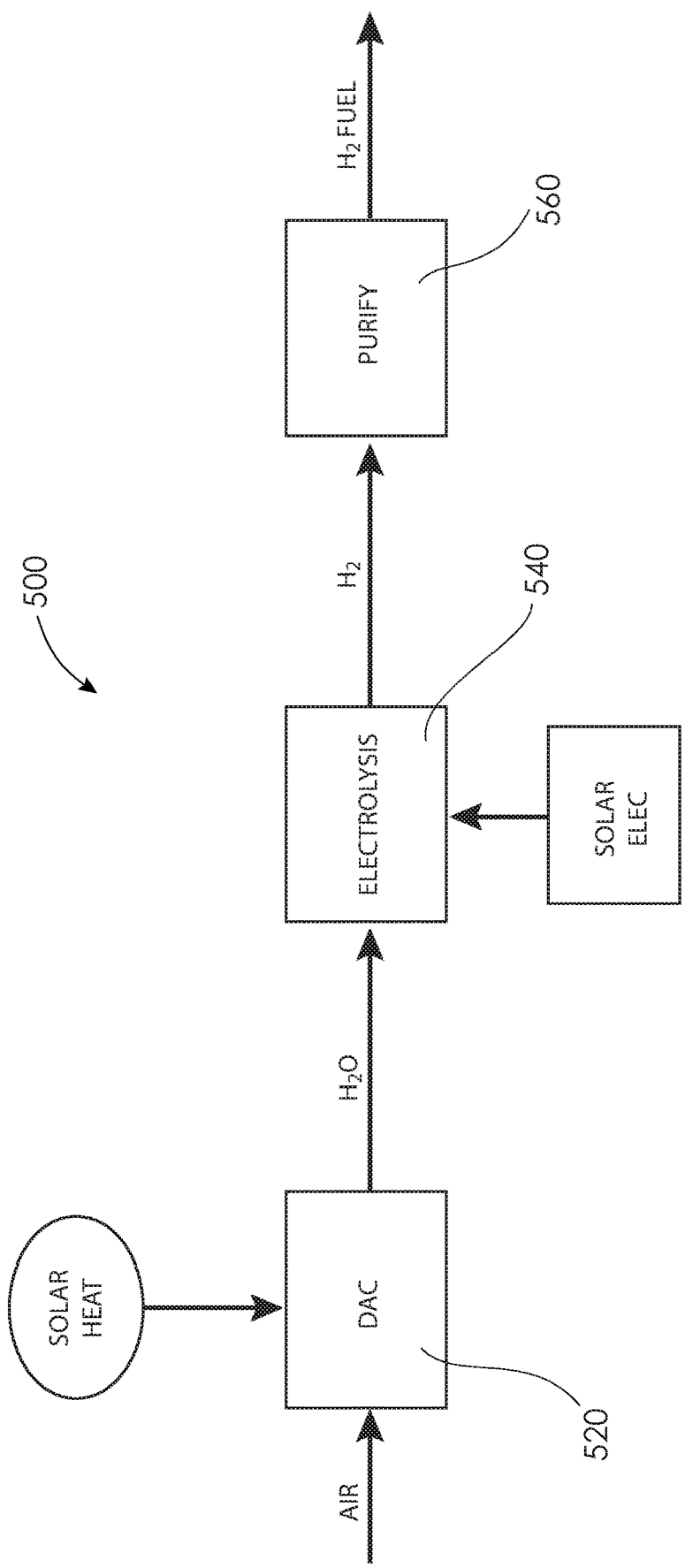
FIG. 4 is a schematic of a process flow sheet for a method and system for the production of hydrogen according to a further aspect of the invention.

As seen in FIG. 4 there is a hydrogen production system 500 of yet another aspect of the invention for producing hydrogen. In this embodiment the hydrogen produced is in the form of hydrogen fuel for fuel cell vehicles. It will be understood that the hydrogen produced from this aspect of the technology may have other uses including but not limited to fertiliser and ammonia production, production of chemicals including hydrochloric acid, pharmaceuticals, semiconductor manufacturing, petroleum refining, hydrogenation, reduction of metallic ores, welding, cryogenics, methanol production, and glass purification.

The hydrogen fuel production system 500 of this embodiment generally comprises:
1. a water capture module 520 for directly capture water from air to provide water in a liquid form;
2. an electrolysis module 540 for electrolysis of the liquid water to produce hydrogen;
3. a purifying module 560 for purifying the hydrogen from the electrolysis module 540 to provide hydrogen fuel.

In this embodiment the water capture module 520 and the electrolysis module 540 are of substantially the same construction as the corresponding modules of the renewable methane production system 100. The hydrogen fuel production system 50 departs insofar as it includes the purifying module 560 which in this embodiment includes a purifying filter (not shown) for filtering the hydrogen produced by the electrolysis module 540. The purifying module 560 thus filters the hydrogen produced by the electrolysis module 540 to obtain hydrogen fuel at purity levels required for fuel cell vehicles. In another departure from the renewable methane production system 100, the electrolysis module 540 relies primarily on the water capture module 520 for its supply of the liquid water.

Now that a preferred embodiment of a renewable methane production module and other aspects of the invention have been described it will be apparent to those skilled in the art that it has the following advantages:
1. the production module in production of renewable methane is powered solely by renewable energy sources and in particular solar energy;
2. the renewable methane production module and the other production systems are efficient in harnessing waste heat from the Sabatier reactor to assist with direct capture of carbon dioxide from atmosphere;
3. the production module exploits the production of steam or liquid water in the Sabatier reactor for return to the electrolyser in the production of hydrogen;
4. the production module in its preferred orientation of solar panels more effectively harnesses solar energy increasing utilisation of the electrolyser for extended production of hydrogen;
5. both production systems in the production of renewable methane and hydrogen are powered or derived from renewable energy sources and in particular solar energy.

Those skilled in the art will appreciate that the invention as described herein is susceptible to variations and modifications other than those specifically described. For example, the specific number and configuration of the solar panels of the production module may vary from that described. The direct capture of water and/or carbon dioxide from atmosphere may be different to the MOF or other technologies of the preferred embodiment. For example, the direct capture of water from air may be effected by refrigeration using a reverse cycle air-conditioning system which is effective in releasing water from air in a liquid form. In this variation, the waste heat from the Sabatier reaction may be harnessed in refrigeration of the air to release the liquid water. In another example, evacuated tubes may be used as an alternative heat source for releasing carbon dioxide from the absorbent material of the carbon dioxide extractor. In the context of the production of renewable methane, the liquid water from the Sabatier reactor need not be recirculated to the electrolysis module. It is to be understood that references to solar panels extends to printed solar such as thin film PV.

It is to be understood that any acknowledgement of prior art in this specification is not to be taken as an admission that this prior art forms part of the common general knowledge as at the priority date of the claims.

All such variations and modifications are to be considered within the scope of the present invention the nature of which is to be determined from the foregoing description.

The invention claimed is:

1. A renewable methane production module comprising:
   a water capture generator designed for directly capturing water from atmosphere to provide water in a liquid form, the water capture generator including an absorbent material designed to be exposed to atmosphere for directly absorbing water from the atmosphere onto the absorbent material;
   an electrolyser operatively coupled to the water capture generator for receiving the liquid water, the electrolyser being effective in electrolysis of the liquid water to produce hydrogen;
   a carbon dioxide extractor for extracting carbon dioxide from atmosphere, the carbon dioxide extractor being configured for directly capturing carbon dioxide from atmosphere using a metal-organic framework (MOF) capable of directly absorbing carbon dioxide from the atmosphere; and
   an exothermic reactor operatively coupled to the electrolyser, said exothermic reactor (a) configured for reacting hydrogen from the electrolyser with carbon dioxide from the carbon dioxide extractor to produce renewable methane in a Sabatier reaction, and (b) operatively coupled to a heat exchanger designed to exchange heat derived from the production of renewable methane with the carbon dioxide extractor to heat the MOF of said extractor to release the absorbed carbon dioxide from the absorbent structure.

2. A renewable methane production module as claimed in claim 1, wherein the water capture generator also includes heating means designed to adsorb heat from a renewable energy source and transfer it to the absorbent material to release the absorbed water from the absorbent material to provide the liquid water for the electrolyser.

3. A renewable methane production module as claimed in claim 1, also comprising an electricity generating assembly powered by a renewable energy source, said electricity generating assembly configured to provide electricity for powering the electrolyser in electrolysis of the atmospheric water in the production of hydrogen.

4. A renewable methane production module as claimed in claim 3, wherein the electricity generating assembly includes a plurality of solar panels operatively coupled to an inverter for production of the electricity for powering the electrolyser, the solar panels being in the form of solar photovoltaic (PV) panels arranged in an elongate bank of panels.

5. A renewable methane production module as claimed in claim 4, wherein:
   the bank of solar PV panels are located in two rows on respective of opposing faces of a solar framework structure which is oriented in a generally magnetic North to South direction; and
   the solar framework structure is in cross-section shaped in the form of an isosceles triangle having each of the two rows of PV panels mounted to respective of leg-sides of the solar framework structure for increased solar exposure for said solar panels.

6. A renewable methane production module as claimed in claim 1, wherein:
   the heat exchanger is operatively coupled to the electrolyser wherein steam produced from the exothermic reactor exchanges heat with the carbon dioxide extractor to promote the release of the absorbed carbon dioxide; and
   said steam is condensed to provide liquid water to the electrolyser for the production of hydrogen.

7. A renewable methane production module as claimed in claim 1, wherein:
   the water capture generator is configured for directly capturing water from atmosphere using a MOF or other absorbent structure capable of directly absorbing water from the atmosphere; and
   the heat exchanger associated with the exothermic reactor being operatively coupled to the water capture generator to heat the absorbent structure of said water generator to release the absorbed water from the absorbent material.

8. A renewable methane production module as claimed in claim 7, wherein:
   the water capture generator is operatively coupled to the carbon dioxide extractor; and
   dehumidified air from the water capture generator is received by the carbon dioxide extractor for extracting carbon dioxide from the dehumidified air.

9. A renewable methane production module as claimed in claim 7, wherein the carbon dioxide extractor is operatively coupled to the heat exchanger associated with the exothermic reactor to heat the absorbent structure of the carbon dioxide extractor to release the absorbed carbon dioxide.

10. A renewable methane production module as claimed in claim 1, wherein the renewable methane production module is one of a plurality of said production modules, said production modules are co-located and together form a renewable methane production plant.

11. A method of producing renewable methane comprising the steps of:
   directly capturing water from air to provide water in a liquid form, said step of directly capturing water involving exposing air to an absorbent material to absorb water from the air onto the absorbent material;
   producing hydrogen by electrolysis of the liquid water;
   extracting carbon dioxide by directly capturing carbon dioxide from air using a metal-organic framework (MOF) capable of directly absorbing carbon dioxide from air; and
   reacting the hydrogen with the directly captured carbon dioxide in an exothermic Sabatier reaction to produce renewable methane, the absorbed carbon dioxide being released from the MOF by heating it via heat derived from the exothermic reaction in production of renewable methane.

12. A method as claimed in claim 11 wherein said step also includes:
   i) releasing the absorbed water from the absorbent material by heating it, and
   ii) condensing the released water by cooling it to provide the liquid water.

13. A method as claimed in claim 11, wherein the step of producing hydrogen involves:
   i) generating electricity via a renewable energy source, and
   ii) using the electricity to power the electrolysis of the liquid water for the production of hydrogen.

14. A method as claimed in claim 11, also comprising the step of recirculating liquid water produced from the reaction between hydrogen and carbon dioxide for electrolysis in the production of hydrogen.

15. A method as claimed in claim 14, wherein the recirculated liquid water is combined with the liquid water directly captured from air for electrolysis in the production of hydrogen.

* * * * *